United States Patent
Liu et al.

(10) Patent No.: US 10,157,693 B2
(45) Date of Patent: Dec. 18, 2018

(54) NEUTRON MODERATION MATERIAL

(71) Applicant: NEUBORON MEDTECH LTD., Nanjing, Jiangsu (CN)

(72) Inventors: Yuan-Hao Liu, Jiangsu (CN); Wei-Lin Chen, Jiangsu (CN)

(73) Assignee: NEUBORON MEDTECH LTD., Nanjing, Jiangsu (CN)

( * ) Notice: Subject to any disclaimer, the term of this patent is extended or adjusted under 35 U.S.C. 154(b) by 0 days.

(21) Appl. No.: 15/952,592

(22) Filed: Apr. 13, 2018

(65) Prior Publication Data

US 2018/0233246 A1   Aug. 16, 2018

Related U.S. Application Data

(63) Continuation of application No. PCT/CN2016/089734, filed on Jul. 12, 2016.

(30) Foreign Application Priority Data

Oct. 15, 2015 (CN) .......................... 2015 1 0665812

(51) Int. Cl.
*G21F 1/08* (2006.01)
*G21F 1/00* (2006.01)
(Continued)

(52) U.S. Cl.
CPC .................. *G21K 1/10* (2013.01); *A61N 5/10* (2013.01); *G21F 1/08* (2013.01);
(Continued)

(58) Field of Classification Search
USPC ................................ 250/505.1, 515.1, 518.1
See application file for complete search history.

(56) References Cited

U.S. PATENT DOCUMENTS 4,303,553 A * 12/1981 Aoki ....................... C04B 14/40
106/682
5,814,824 A * 9/1998 Hamby .................... G21D 1/02
250/506.1
(Continued)

FOREIGN PATENT DOCUMENTS

| CN | 102260812 A | 11/2011 |
| CN | 104511096 A | 4/2015 |

(Continued)

OTHER PUBLICATIONS

International Search Report of PCT/CN2016/089734, dated Sep. 22, 2016.
(Continued)

*Primary Examiner* — Bernard Souw
(74) *Attorney, Agent, or Firm* — Locke Lord LLP; Tim Tingkang Xia, Esq.

(57) ABSTRACT

A neutron moderation material for use in a BNCT beam shaping assembly. The neutron moderation material comprises three elements, i.e., Mg, Al, and F, wherein the mass fraction of the Mg element is 3.5%-37.1%, the mass fraction of the Al element is 5%-90.4%, and the mass fraction of the F element is 5.8%-67.2%; the sum of the weights of the Mg, Al, and F elements is 100% of the total weight of the neutron moderation material. The neutron moderation material may be doped with a small amount of $^6$Li-containing substances, and the addition of the $^6$Li-containing substances effectively decreases the content of γ-rays in epithermal neutron beams.

20 Claims, 1 Drawing Sheet

(51) Int. Cl.
*G21K 1/10* (2006.01)
*A61N 5/10* (2006.01)
(52) U.S. Cl.
CPC ............... *A61N 2005/109* (2013.01); *A61N 2005/1095* (2013.01); *G21Y 2004/10* (2013.01)

(56) References Cited

U.S. PATENT DOCUMENTS

| | | | |
|---|---|---|---|
| 7,250,119 B2 | 7/2007 | Sayala | |
| 7,327,821 B2* | 2/2008 | Ishihara | G21F 1/103 250/505.1 |
| 2014/0103230 A1 | 4/2014 | Kang | |
| 2015/0207029 A1 | 7/2015 | Shur et al. | |

FOREIGN PATENT DOCUMENTS

| | | |
|---|---|---|
| CN | 104548388 A | 4/2015 |
| CN | 104575653 A | 4/2015 |
| CN | 104726731 A | 6/2015 |
| WO | 2015111586 A1 | 7/2015 |

OTHER PUBLICATIONS

International Search Report of PCT/CN2016089734, dated Jul. 26, 2018.

* cited by examiner

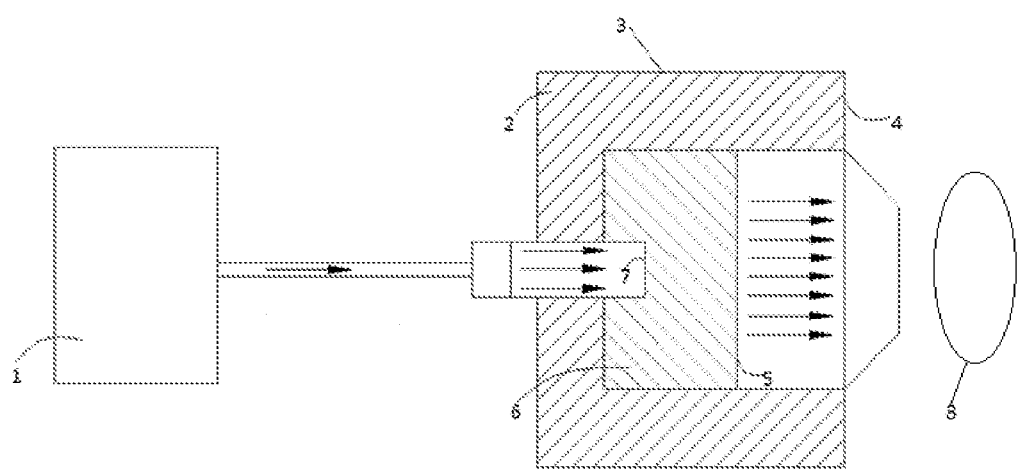

NEUTRON MODERATION MATERIAL

RELATED APPLICATION INFORMATION

This application is a continuation of International Application No. PCT/CN2016/089734, filed on Jul. 12, 2016, which claims priority to Chinese Patent Application No. 201510665812.2, filed on Oct. 15, 2015, the disclosures of which are hereby incorporated by reference.

FIELD OF THE DISCLOSURE

The present disclosure relates to a radiation moderation material, and, more particularly, to a neutron moderation material.

BACKGROUND OF THE DISCLOSURE

With the generation of accelerators, boron neutron capture therapy (BNCT) technology entered a stage of rapid development. Neutrons with different energies produced by the proton produced by the accelerator interacting with the target or generated through the nuclear reaction. These neutrons are moderated by a beam shaping assembly to epithermal neutrons at a key energy level, and further become thermal neutrons after into the human body. The thermal neutrons react with the boron-containing pharmaceuticals in the tumor cells, and the radiation energy thereof can destroy the tumor cells. The killing range is restricted at the cells' level and there is almost no harm to normal tissues.

The neutrons produced from the target have a wide range of energy distributions including thermal neutrons, epithermal neutrons and fast neutrons, the radiation beam also includes γ rays which do not contribute to the treatment and result in a larger proportion of nonselective dose deposition in normal tissue, and the more the proportion of nonselective dose deposition in normal tissue is, the greater the damage to normal tissue is. One of the applications of moderation materials in beam shaping assembly as the neutron moderation material is the key to improving beam quality and reducing the amount of unwanted rays in the treatment. Therefore, the moderation material in the beam shaping assembly becomes the hotspot in the field of BNCT technology, and the advantages and disadvantages of neutron moderation material are mainly reflected by the neutron beam quality. The neutron beam quality is divided into air beam quality and prosthesis beam quality, wherein the air beam quality can be evaluated synthetically by epithermal neutron beam flux, fast neutron contamination, γ ray contamination, thermal to epithermal neutron flux ratio and neutron forwardness, while the prosthesis beam quality is reflected by the dose distribution of the beam in the prosthesis and the therapeutic effect of the beam in the prosthesis. In addition to the advantage depth (AD), advantage depth dose rate (ADDR) and advantage dose rate (AR) and treatment time as prosthesis beam quality factors, using 30.0 RBE-Gy treatable depth can better reflect the maximum advantage depth of cancer.

The screening of neutron moderation materials for the prosthesis beam quality has not been found, yet.

The statements in this section merely provide background information related to the present disclosure and may not constitute prior art.

SUMMARY

One aspect of the present disclosure is to provide a neutron moderation material having a better prosthesis beam quality, more particularly, having a better advantage depth in the tumor treatment.

In another aspect of the present disclosure is to reduce γ ray contamination in an epithermal neutron beam by adding a certain amount of Li-containing material to the neutron moderation material.

In order to achieve the objects and other advantages, an aspect of the present disclosure provides a neutron moderation material includes: Mg element, Al element and F element, wherein, the weight percentage of the three elements of Mg, Al and F accounts for the neutron moderation material is $3.5\% \leq Mg \leq 37.1\%$, $5.0\% \leq Al \leq 90.4\%$, $5.8\% \leq F \leq 67.2\%$, respectively. And the sum of the weights of the three elements of Mg, Al and F is 100% of the total weight of the neutron moderation material.

Implementations of this aspect may include one or more of the following features.

The neutron moderation material is added with a $^6$Li-containing substances to reduce γ ray contamination, wherein the addition amount of the $^6$Li-containing substances accounts for 0.1% to 10% in percentage by weight of the neutron moderation material. Preferably, the neutron moderation material is added with natural LiF to reduce γ ray contamination, wherein the amount of LiF is 0.1% to 10% of the total weight of the neutron moderation material.

More particularly, in the neutron moderation material, the neutron moderation material has a density is 60% to 100% of the theoretical density.

More particularly, in the neutron moderation material, the material composition of the neutron moderation material is $MgF_2$ and Al.

More particularly, in the neutron moderation material, the relationship between the ratio of the density of the neutron moderation material to the theoretical density and the weight percentage of Al element in the neutron moderation material is selected in the following groups: the weight percentage of the Al element to the neutron moderation material is $35\% \leq Al \leq 70\%$ when the density of the neutron moderation material is 60% of the theoretical density; the weight percentage of the Al element to the neutron moderation material is $50\% \leq Al \leq 80\%$ when the density of the neutron moderation material is 80% of the theoretical density; the weight percentage of the Al element to the neutron moderation material is $65\% \leq Al \leq 90\%$ when the density of the neutron moderation material is the theoretical density.

More particularly, in the neutron moderation material, the relationship between the ratio of the density of the neutron moderation material to the theoretical density and the weight ratio of Al to $MgF_2$ is selected in the following groups: the weight ratio of Al to $MgF_2$ is 11:9 when the density of the neutron moderation material is 60% of the theoretical density; the weight ratio of Al to $MgF_2$ is 13:7 when the density of the neutron moderation material is 80% of the theoretical density; the weight ratio of Al to $MgF_2$ is 4:1 when the density of the neutron moderation material is the theoretical density.

More particularly, in the neutron moderation material, the neutron moderation material is disposed in a beam shaping assembly in the form of stacked or mixed powder compact or mixed powder sinter serving as a moderator of the beam shaping assembly.

Wherein the beam shaping assembly further comprises a reflector surrounding the moderator, a thermal neutron absorber adjoining to the moderator, and a radiation shield disposed within the beam shaping assembly.

More particularly, the beam shaping assembly is used for accelerator-based neutron capture therapy, and the accelerator-based neutron capture therapy comprises an accelerator, a charged-particle beam accelerated by the accelerator, a beam inlet for the charged-particle beam passing through, a neutron generating portion for generating a neutron beam by nuclear reaction with the charged-particle beam, a beam shaping assembly for adjusting the beam flux and quality of the neutron beam generated by the neutron generating portion, and a beam outlet adjoining to the beam shaping assembly, wherein the neutron generating portion is accommodated in the beam shaping assembly.

In another aspect of the present disclosure provides a neutron moderation material includes: Mg element, Al element and F element, the sum of the weights of the weights of the Mg, Al and F elements is 100% of the total weight of the neutron moderation material, the neutron moderation material is added with $^6$Li-containing substances to reduce γ ray contamination, wherein the addition amount of the $^6$Li-containing substances accounts for 0.1% to 10% in percentage by weight of the neutron moderation material.

More particularly, the density of the neutron moderation material is 60% to 100% of the theoretical density.

More particularly, the material composition of the neutron moderation material is $MgF_2$ and Al.

More particularly, the relationship between the ratio of the density of the neutron moderation material to the theoretical density and the weight percentage of Al element in the neutron moderation material is selected in the following groups:the weight percentage of the Al element to the neutron moderation material is 35%≤Al≤70% when the density of the neutron moderation material is 60% of the theoretical density; the weight percentage of the Al element to the neutron moderation material is 50%≤Al≤80% when the density of the neutron moderation material is 80% of the theoretical density; the weight percentage of the Al element to the neutron moderation material is 65%≤Al≤90% when the density of the neutron moderation material is the theoretical density.

More particularly, the relationship between the ratio of the density of the neutron moderation material to the theoretical density and the weight ratio of Al to $MgF_2$ is selected in the following groups: the weight ratio of Al to $MgF_2$ is 11:9 when the density of the neutron moderation material is 60% of the theoretical density; the weight ratio of Al to $MgF_2$ is 13:7 when the density of the neutron moderation material is 80% of the theoretical density; the weight ratio of Al to $MgF_2$ is 4:1 when the density of the neutron moderation material is the theoretical density.

More particularly, the $^6$Li-containing substances are LiF.

In yet another aspect of the present disclosure provides a neutron moderation material includes: Mg element, Al element and F element, the sum of the weights of the weights of the Mg, Al and F elements is 100% of the total weight of the neutron moderation material, Mg element, Al element and F element make up the substance of Al, $MgF_2$ and $AlF_3$, and one or more of Al, $MgF_2$ and $AlF_3$ form a moderator in the form of stacked or mixed powder compact or mixed powder sinter.

More particularly, the moderator consists of Al and $MgF_2$

More particularly, the weight ratio of Al to $MgF_2$ is between 1:19 to 9:1.

More particularly, the neutron moderation material is added with $^6$Li-containing substances to reduce γ ray contamination, wherein the addition amount of the $^6$Li-containing substances accounts for 0.1% to 10% in percentage by weight of the neutron moderation material.

The present disclosure includes at least the following benefits: the neutron moderation material including three elements of Al, Mg, and F enables the neutron beam to have excellent prosthetic beam quality, such as the advantage depth and 30.0 RBE-Gy advantage depth, improving the advantage depth of tumor of BNCT; In addition, if the neutron moderation material is added with a certain amount of $^6$LiF, the neutron moderation material can effectively reduce the γ ray contamination in the epithermal neutron beam, and effectively improve the quality of air beam without affecting the quality of the prosthetic beam.

Other advantages, objects, and features of the disclosure will be apparent to those skilled in the art from the following description, taken in part by the research and practice of the disclosure.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

FIG. 1 is a schematic plane diagram of accelerator-based BNCT.

The drawings described herein are for illustrative purposes only of selected embodiments and not all possible implementations, and are not intended to limit the scope of the present disclosure. Corresponding reference numerals indicate corresponding parts throughout the several views of the drawings.

DETAILED DESCRIPTION

The present disclosure will now be described in further detail with reference to the accompanying drawings in order to enable those skilled in the art to practice with reference to the specification.

The following description of the preferred embodiments is merely exemplary in nature and is in no way intended to limit the invention, its application, or uses.

It should be understood that the terms "having", "comprising", and "including" as used herein do not exclude the presence or addition of one or more other ingredients or combinations thereof.

The beam quality of the prosthesis 8 directly affects the therapeutic effect, wherein the element composition of the prosthesis 8 affects the neutron drifting and the therapeutic dose, and the prosthesis used in the present disclosure is Modified Snyder head phantom. The following three parameters can be used to evaluate the therapeutic effect of neutron beam:

1. Advantage Depth:

Tumor dose is equal to the depth of the maximum dose of the normal tissue. Dose of the tumor cells at a position behind the depth is less than the maximum dose of the normal tissue, that is, boron neutron capture loses its advantages. The advantage depth indicates the penetrability of the neutron beam. Calculated by cm, the larger the advantage depth is, the lager the treatable tumor depth is.

2. Advantage Depth Dose Rate:

The advantage depth dose rate is the tumor dose rate of the advantage depth and also equal to the maximum dose rate of the normal tissue. Since the total dose of the normal tissue is a factor capable of influencing the total dose given to the tumors, so the advantage depth dose rate affects the length of treatment time. The greater the advantage depth dose rate is, the shorter the irradiation time for giving a certain dose to the tumors is, calculated by Gy/mA-min.

3. Advantage Dose Rate:

From the brain surface to the advantage depth, the average dose rate received by tumor and normal tissue is called as the advantage dose rate. The calculation of average dose can be obtained by integrating the dose-depth curve. The greater the advantage dose rate, the better the therapeutic effect of the neutron beam.

Due to photons and neutrons express different biological doses respectively, therefore, the fast neutron dose, the thermal neutron dose and the photon dose should be respectively multiplied with the relative biological effects (RBE) of the different tissues to obtain the equivalent dose.

The present disclosure selects the treatment depth of the beam quality of the prosthesis 8 as the evaluation criterion, and when the dose is 30.0 RBE-Gy, it is more effective to eliminate the cancer cells, therefore, we use 30.0 RBE-Gy treatable depth as basis for judgment, more direct than the advantage depth. The parameters used to evaluate the beam quality of the prosthesis Bare as follows:

1. Advantage Depth:

As mentioned before, the larger the advantage depth is, the lager the treatable tumor depth is, calculated by cm.

2. 30.0 RBE-Gy Treatable Depth (TD):

30.0 RBE-Gy treatable depth represents the maximum depth that the tumor dose can reach 30.0 RBE-Gy along the axis of the beam in the prosthesis, calculated by cm. The administration dose of 30.0 RBE-Gy ensures a fatal attack on cancer cells. The larger the 30.0 RBE-Gy treatable depth, the lager the depth of the tumor that can be effectively killed.

In order to achieve the object of the present disclosure, the neutron moderation material comprises Mg element, Al element and F element, wherein, the weight percentage of Mg element, Al element and F element accounts for the neutron moderation material is $3.5\% \leq Mg \leq 37.1\%$, $5.0\% \leq Al \leq 90.4\%$, $5.8\% \leq F \leq 67.2\%$, respectively. And the sum of the weights of the Mg, Al and F elements is 100% of the total weight of the neutron moderation material. The combination and ratio can increase the advantage depth and 30.0 RBE-Gy treatable depth, so that the beam passing through the neutron moderation material has better prosthesis beam quality.

The neutron moderation material is added with $^6$Li-containing substances to reduce γ ray contamination, wherein the addition amount of the $^6$Li-containing substances is 0.1% to 10% of the total weight of the neutron moderation material. The addition of the $^6$Li-containing substances can effectively reduce the γ ray contamination while ensuring that the neutron moderation material has better prosthesis beam quality.

The density of the neutron moderation material is 60% to 100% of the theoretical density. If the density is less than 60% of theoretical density, the volume of the moderation body composed of the moderation material become larger and the beam flux passing through the moderation body decreases, resulting in prolonged treatment time.

Wherein the material composition of the neutron moderation material may be $MgF_2$ and Al.

In the neutron moderation material, the relationship between the ratio of the density of the neutron moderation material to the theoretical density and the weight percentage of Al element in the neutron moderation material is selected in the following groups: the weight percentage of the Al element to the neutron moderation material is $35\% \leq Al \leq 70\%$ when the density of the neutron moderation material is 60% of the theoretical density; the weight percentage of the Al element to the neutron moderation material is $50\% \leq Al \leq 80\%$ when the density of the neutron moderation material is 80% of the theoretical density; the weight percentage of the Al element to the neutron moderation material is $65\% \leq Al \leq 90\%$ when the density of the neutron moderation material is the theoretical density. Under the above conditions, 30.0 RBE-Gy can reach a depth greater than 7 cm.

In the neutron moderation material, the relationship between the ratio of the density of the neutron moderation material to the theoretical density and the weight ratio of Al to $MgF_2$ is selected in the following groups: the weight ratio of Al to $MgF_2$ is 11:9 when the density of the neutron moderation material is 60% of the theoretical density; the weight ratio of Al to $MgF_2$ is 13:7 when the density of the neutron moderation material is 80% of the theoretical density; the weight ratio of Al to $MgF_2$ is 4:1 when the density of the neutron moderation material is the theoretical density. Under the above conditions, 30.0 RBE-Gy of the neutron moderation material at the corresponding density can reach the maximum.

The neutron moderation material is disposed in the beam shaping assembly 3 in the form of stacked or mixed powder compact or mixed powder sinter serving as a moderator 6 of the beam shaping assembly 3.

Wherein the beam shaping assembly 3 further includes a reflector 2 surrounding the moderator 6, a thermal neutron absorber 5 adjoining to the moderator 6, and a radiation shield 4 disposed within the beam shaping assembly 3.

The beam shaping assembly 3 is used for accelerator-based neutron capture treatment therapy, and the accelerator-based neutron capture treatment therapy includes an accelerator 1, a charged-particle beam accelerated by the accelerator 1, a beam inlet for the charged particle beam passing through, a neutron generating portion 7 for generating a neutron beam by nuclear reaction with the charged-particle beam, a beam shaping assembly 3 for adjusting the beam flux and quality of the neutron beam generated by the neutron generating portion 7, and a beam outlet adjoining to the beam shaping assembly 3, wherein the neutron generating portion 7 is accommodated in the beam shaping assembly 3.

Experiments prove that the material containing the three elements of Al, Mg and F as the neutron moderation material of the beam shaping assembly 3 in BNCT can effectively improve the prosthesis beam quality. There are several types of material composition that contain these three elements, but are not limited to the following: 1. Al and $MgF_2$; 2. $AlF_3$ and $MgF_2$; 3. Al, $AlF_3$, and $MgF_2$; 4. sinter containing the three elements of Al, Mg, and F. These substances containing the three elements of Al, Mg, and F can be mixed evenly or be stacked by different substances. The following Examples 1, 2, 3 and 6 were completed on the basis of a 72.5 cm thickness of the neutron moderation material, and the remaining examples were completed on the basis of a 60 cm thickness of the neutron moderation material. Here, reference the thickness of the neutron moderation material is only to illustrate the beneficial effect of the neutron moderation material, not to be to limit the thickness of the neutron moderation material.

EXAMPLES

Example 1

Selecting different parts by weight of Al and $MgF_2$. When the density of the mixed powder compact is 60% of the theoretical density, the advantage depth and the depth of the tumor 30 RBE-Gy were calculated by MCNP simulation. The results are shown in Table 1:

TABLE 1 the prosthesis beam quality when the density of Al and
MgF$_2$ mixed powder compact is 60% of the theoretical density

| Weight ratio of Al to MgF$_2$ | Contents of three elements | | | Advantage depth (cm) | Depth of tumor 30RBE-Gy (cm) |
|---|---|---|---|---|---|
| | Al | Mg | F | | |
| 5:95 | 5.0% | 37.1% | 57.9% | 12.13 | 5.61 |
| 10:90 | 10.0% | 35.1% | 54.9% | 12.35 | 6.17 |
| 15:85 | 15.0% | 33.2% | 51.8% | 12.50 | 6.30 |
| 20:80 | 20.0% | 31.2% | 48.8% | 12.57 | 6.60 |
| 25:75 | 25.0% | 29.3% | 45.7% | 12.66 | 6.79 |
| 30:70 | 30.0% | 27.3% | 42.7% | 12.72 | 6.94 |
| 35:65 | 35.0% | 25.4% | 39.6% | 12.61 | 7.17 |
| 40:60 | 40.0% | 23.4% | 36.6% | 12.85 | 7.16 |
| 45:55 | 45.0% | 21.5% | 33.5% | 12.98 | 7.20 |
| 50:50 | 50.0% | 19.5% | 30.5% | 12.82 | 7.15 |
| 55:45 | 55.0% | 17.6% | 27.4% | 12.96 | 7.34 |
| 60:40 | 60.0% | 15.6% | 24.4% | 13.05 | 7.23 |
| 65:35 | 65.0% | 13.7% | 21.3% | 12.86 | 7.24 |
| 70:30 | 70.0% | 11.7% | 18.3% | 13.05 | 7.05 |
| 75:25 | 75.0% | 9.8% | 15.2% | 13.09 | 6.88 |
| 80:20 | 80.0% | 7.8% | 12.2% | 13.11 | 6.31 |
| 85:15 | 85.0% | 5.9% | 9.1% | 12.83 | 5.73 |
| 90:10 | 90.0% | 3.9% | 6.1% | 12.78 | 4.95 |

Example 2

Selecting different parts by weight of Al and MgF$_2$. the advantage depths and the depths of the tumor 30 RBE-Gy of the neutron moderation material of the Al and MgF$_2$ mixed powder compact with a density is 80% of the theoretical density and the Al and MgF$_2$ mixed powder sinter with a density is 80% of the theoretical density were calculated by MCNP simulation, respectively. In the case of the same mixture composition and ratio, there is no difference in the prosthesis beam quality between the mixed powder sinter mixed evenly and the mixed powder compact mixed evenly. The results of the treatment depth and the depth of 30.0 RBE-Gy are shown in Table 2:

TABLE 2 the prosthesis beam quality when the density of Al
and MgF$_2$ mixture is 80% of the theoretical density

| Weight ratio of Al to MgF$_2$ | Contents of the three elements of | | | Advantage depth (cm) | Depth of tumor 30RBE-Gy (cm) |
|---|---|---|---|---|---|
| | Al | Mg | F | | |
| 5:95 | 5.0% | 37.1% | 57.9% | 11.90 | 4.00 |
| 10:90 | 10.0% | 35.1% | 54.9% | 11.72 | 4.28 |
| 15:85 | 15.0% | 33.2% | 51.8% | 11.72 | 4.95 |
| 20:80 | 20.0% | 31.2% | 48.8% | 12.05 | 5.23 |
| 25:75 | 25.0% | 29.3% | 45.7% | 12.17 | 5.54 |
| 30:70 | 30.0% | 27.3% | 42.7% | 12.23 | 5.75 |
| 35:65 | 35.0% | 25.4% | 39.6% | 12.42 | 6.17 |
| 40:60 | 40.0% | 23.4% | 36.6% | 12.34 | 6.55 |
| 45:55 | 45.0% | 21.5% | 33.5% | 12.50 | 6.85 |
| 50:50 | 50.0% | 19.5% | 30.5% | 12.78 | 7.24 |
| 55:45 | 55.0% | 17.6% | 27.4% | 12.78 | 7.20 |
| 60:40 | 60.0% | 15.6% | 24.4% | 12.76 | 7.33 |
| 65:35 | 65.0% | 13.7% | 21.3% | 12.94 | 7.53 |
| 70:30 | 70.0% | 11.7% | 18.3% | 12.96 | 7.44 |
| 75:25 | 75.0% | 9.8% | 15.2% | 12.97 | 7.34 |
| 80:20 | 80.0% | 7.8% | 12.2% | 13.25 | 7.34 |
| 85:15 | 85.0% | 5.9% | 9.1% | 13.17 | 6.92 |
| 90:10 | 90.0% | 3.9% | 6.1% | 13.26 | 6.67 |

Example 3

Selecting different parts by weight of Al and MgF$_2$. When the density of the mixed powder sinter is the theoretical density, the advantage depth and the depth of the tumor 30 RBE-Gy were calculated by MCNP simulation. The results are shown in Table 3:

TABLE 3 the prosthesis beam quality when the density of Al and
MgF$_2$ mixed powder sinter is the theoretical density

| Weight ratio of Al to MgF$_2$ | Contents of the three elements of | | | Advantage depth (cm) | Depth of tumor 30RBE-Gy (cm) |
|---|---|---|---|---|---|
| | Al | Mg | F | | |
| 5:95 | 5.0% | 37.1% | 57.9% | 10.93 | 2.34 |
| 10:90 | 10.0% | 35.1% | 54.9% | 10.83 | 2.78 |
| 15:85 | 15.0% | 33.2% | 51.8% | 11.31 | 3.38 |
| 20:80 | 20.0% | 31.2% | 48.8% | 11.43 | 3.88 |
| 25:75 | 25.0% | 29.3% | 45.7% | 11.60 | 4.19 |
| 30:70 | 30.0% | 27.3% | 42.7% | 11.92 | 4.47 |
| 35:65 | 35.0% | 25.4% | 39.6% | 11.97 | 5.33 |
| 40:60 | 40.0% | 23.4% | 36.6% | 12.19 | 5.63 |
| 45:55 | 45.0% | 21.5% | 33.5% | 12.08 | 5.94 |
| 50:50 | 50.0% | 19.5% | 30.5% | 12.52 | 6.40 |
| 55:45 | 55.0% | 17.6% | 27.4% | 12.58 | 6.96 |
| 60:40 | 60.0% | 15.6% | 24.4% | 12.49 | 6.89 |
| 65:35 | 65.0% | 13.7% | 21.3% | 12.64 | 7.29 |
| 70:30 | 70.0% | 11.7% | 18.3% | 12.84 | 7.26 |
| 75:25 | 75.0% | 9.8% | 15.2% | 12.99 | 7.45 |
| 80:20 | 80.0% | 7.8% | 12.2% | 13.06 | 7.93 |
| 85:15 | 85.0% | 5.9% | 9.1% | 13.09 | 7.45 |
| 90:10 | 90.0% | 3.9% | 6.1% | 13.10 | 7.26 |

Example 4

Selecting different parts by weight of Al and MgF$_2$, Al and MgF$_2$ were combined to form the neutron moderation material in a stacked form. When the density of the neutron moderation material is the theoretical density, the advantage depth and the depth of the tumor 30 RBE-Gy were calculated by MCNP simulation. The results are shown in Table 4:

TABLE 4 the prosthesis beam quality when the neutron moderation
material is composed of Al and MgF$_2$ in the stacked
form with the density is the theoretical density

| Contents of the three elements of | | | Advantage depth (cm) | Depth of tumor 30RBE-Gy (cm) |
|---|---|---|---|---|
| Al | Mg | F | | |
| 7.2% | 36.2% | 56.6% | 10.82 | 2.74 |
| 14.6% | 33.3% | 52.1% | 11.58 | 3.42 |
| 22.2% | 37.3% | 47.4% | 11.59 | 3.67 |
| 30.0% | 27.3% | 42.7% | 12.15 | 4.35 |
| 38.0% | 24.2% | 37.8% | 12.01 | 5.04 |
| 46.2% | 21.0% | 32.8% | 12.40 | 5.50 |
| 54.6% | 17.7% | 27.7% | 12.97 | 6.17 |
| 63.2% | 14.4% | 22.5% | 12.71 | 6.87 |
| 72.0% | 10.9% | 17.1% | 13.12 | 7.11 |
| 81.1% | 7.4% | 11.5% | 13.13 | 7.18 |
| 90.4% | 3.7% | 5.8% | 13.11 | 6.83 |

Example 5

Selecting different parts by weight of AlF$_3$ and MgF$_2$, AlF$_3$ and MgF$_2$ were combined to form a neutron moderation material in a stacked form. When the density of the neutron moderation material is the theoretical density, the advantage depth and the depth of the tumor 30 RBE-Gy were calculated by MCNP simulation. The results are shown in Table 5:

TABLE 5 the prosthesis beam quality when the neutron moderation material is composed of $AlF_3$ and $MgF_2$ in the stacked form with the density is the theoretical density

| Contents of the three elements of | | | Advantage depth | Depth of tumor 30RBE-Gy |
|---|---|---|---|---|
| Al, | Mg | F | (cm) | (cm) |
| 2.5% | 36.0% | 61.5% | 10.84 | 2.58 |
| 5.0% | 33.0% | 62.0% | 10.86 | 2.31 |
| 7.5% | 29.9% | 62.6% | 11.06 | 2.56 |
| 10.1% | 26.8% | 63.1% | 10.99 | 2.77 |
| 12.7% | 23.6% | 63.7% | 11.07 | 2.88 |
| 15.4% | 20.4% | 64.3% | 11.05 | 2.97 |
| 18.0% | 17.1% | 64.9% | 11.22 | 3.11 |
| 20.8% | 13.8% | 65.4% | 11.49 | 3.16 |
| 23.5% | 10.4% | 66.0% | 11.42 | 3.61 |
| 26.4% | 7.0% | 66.6% | 11.73 | 3.72 |
| 29.2% | 3.5% | 67.2% | 11.61 | 3.84 |

Example 6

The γ ray contamination is defined as the γ ray dose associated with a unit epithermal neutron flux, calculated by Gy-cm$^2$/n. Research shows that the $^6$Li-containing substances can effectively reduce the content of γ ray in the neutron beam without reducing the prosthesis beam quality. The $^6$Li-containing substances include but is not limited to $^6$Li Elemental, LiF, $Li_2CO_3$, $Li_2O$ and $Li_2C_2$. In this experiment, natural LiF i used as an example to illustrate the effects of $^6$Li-containing substances on the prosthesis beam quality and γ-ray content. It is well known to those skilled in the art that the inventors here merely uses natural LiF as an example and does not limit the content of $^6$Li in LiF. In addition to the natural LiF, it is also feasible to use other $^6$Li content.

Table 6 shows the effects of adding LiF in amount of 0.1%, 5% and 10% of the neutron moderation material in the Al and $MgF_2$ mixed powder compacts with a density is 80% of the theoretical density in Example 2 on the quality of the prosthesis beam quality and the γ ray contamination, respectively.

TABLE 6

Effects of adding different amounts of LiF on the prosthesis beam quality and γ ray content

| Contents of the three elements of | | | LiF added in an amount of 0.1% of the mass of the neutron moderation material | | | LiF added in an amount of 5% of the mass of the neutron moderation material | | | LiF added in an amount of 10% of the mass of the neutron moderation material | | |
|---|---|---|---|---|---|---|---|---|---|---|---|
| Al | Mg | F | Advantage depth (cm) | Depth of tumor 30RBE-Gy (cm) | γ ray contamination (Gy-cm$^2$/n) | Advantage depth (cm) | Depth of tumor 30RBE-Gy (cm) | γ ray contamination (Gy-cm$^2$/n) | Advantage depth (cm) | Depth of tumor 30RBE-Gy (cm) | γ ray contamination (Gy-cm$^2$/n) |
| 5% | 36.77% | 58.23% | 11.85 | 4.98 | 7.47E-13 | 13.16 | 8.66 | 7.85E-14 | 13.39 | 9.24 | 5.69E-14 |
| 10% | 34.84% | 55.16% | 12.14 | 5.23 | 8.03E-13 | 12.85 | 8.58 | 1.45E-13 | 13.43 | 9.23 | 9.71E-14 |
| 15% | 32.90% | 52.01% | 12.11 | 5.71 | 7.85E-13 | 13.05 | 9.30 | 9.73E-14 | 13.60 | 9.67 | 1.67E-13 |
| 20% | 30.97% | 49.03% | 12.08 | 5.91 | 7.08E-13 | 13.29 | 8.75 | 1.17E-13 | 13.41 | 9.63 | 9.83E-14 |
| 25% | 29.03% | 45.97% | 12.30 | 6.05 | 5.76E-13 | 13.03 | 8.98 | 1.51E-13 | 13.23 | 9.29 | 1.32E-13 |
| 30% | 27.10% | 42.90% | 12.77 | 6.35 | 6.07E-13 | 13.13 | 8.97 | 9.98E-14 | 13.45 | 9.40 | 1.05E-13 |
| 35% | 25.16% | 39.84% | 12.60 | 6.63 | 5.76E-13 | 13.24 | 9.27 | 8.44E-14 | 13.48 | 9.29 | 8.91E-14 |
| 40% | 23.23% | 36.77% | 12.55 | 7.17 | 5.34E-13 | 13.33 | 9.25 | 1.07E-13 | 13.31 | 9.22 | 1.1E-13 |
| 45% | 21.29% | 33.71% | 12.57 | 7.10 | 4.30E-13 | 13.07 | 9.24 | 1.06E-13 | 13.56 | 9.37 | 1.15E-13 |
| 50% | 19.35% | 30.65% | 12.84 | 7.37 | 3.54E-13 | 13.32 | 9.14 | 9.99E-14 | 13.40 | 9.50 | 7.37E-14 |
| 55% | 17.42% | 27.58% | 12.83 | 7.42 | 3.57E-13 | 13.10 | 9.05 | 1.67E-13 | 13.43 | 9.38 | 6.03E-14 |
| 60% | 15.48% | 24.52% | 12.95 | 7.68 | 3.62E-13 | 13.46 | 8.76 | 7.89E-14 | 13.44 | 9.34 | 6.04E-14 |
| 65% | 13.55% | 21.45% | 12.99 | 7.72 | 2.98E-13 | 13.33 | 8.88 | 1.09E-13 | 13.44 | 8.87 | 8.48E-14 |
| 70% | 11.61% | 18.39% | 13.08 | 7.58 | 3.23E-13 | 13.38 | 8.89 | 9.39E-14 | 13.30 | 8.91 | 7.33E-14 |
| 75% | 9.68% | 15.32% | 13.00 | 7.68 | 3.53E-13 | 13.22 | 8.54 | 7.72E-14 | 13.55 | 8.56 | 8.29E-14 |
| 80% | 7.74% | 12.26% | 13.19 | 7.48 | 2.69E-13 | 13.40 | 8.25 | 7.9E-14 | 13.46 | 8.47 | 9.04E-14 |
| 85% | 5.81% | 9.19% | 13.21 | 7.15 | 2.60E-13 | 13.38 | 7.93 | 9.12E-14 | 13.49 | 8.38 | 8.26E-14 |
| 90% | 3.87% | 6.13% | 13.18 | 6.77 | 2.95E-13 | 13.38 | 7.56 | 8.55E-14 | 13.50 | 7.91 | 8.82E-14 |

In order to illustrate the effects of the present disclosure, the inventors provide comparative experiments as follows:

Comparative Example 1

As in Example 1, when the compact substances with a density is 60% of the theoretical density and without adding Al element, that is, the mass fraction of Al is 0%, the advantage depth is 12.24 cm and the depth of the tumor 30 RBE-Gy is 5.39 cm.

Comparative Example 2

As in Example 2, when the compact substances with a density is 80% of the theoretical density and without adding Al element, that is, the mass fraction of Al is 0%, the advantage depth is 11.39 cm and the depth of the tumor 30 RBE-Gy is 3.73 cm.

Comparative Example 3

As in Example 3, when the sinter with a density is the theoretical density and without adding Al element, that is, the mass fraction of aluminum is 0%, the advantage depth is 10.62 cm, and the depth of the tumor 30 RBE-Gy is 1.96 cm.

Comparative Example 4

As in Example 5, when the stacked substances with a density of the theoretical density and without adding Al element, at same time the weight ratio of Mg element is 39%, the advantage depth is 11.1 cm, and the depth of the tumor 30 RBE-Gy is 2.59 cm.

Comparative Example 5

When no LiF is added under the experimental conditions of Example 2, the γ ray contamination in the epithermal neutron ray passing through the neutron moderation material is shown in Table 7.

TABLE 7

γ-ray contamination in the epithermal neutron ray when no LiF added in Al and $MgF_2$ mixture with a density is 80% of the theoretical density

| Contents of the three elements | | | γ ray contamination |
|---|---|---|---|
| Al | Mg | F | (Gy-cm$^2$/n) |
| 5% | 36.77% | 58.23% | 1.17E−12 |
| 10% | 4.84% | 55.16% | 1.13E−12 |
| 15% | 32.90% | 52.01% | 1.08E−12 |
| 20% | 30.97% | 49.03% | 1.01E−12 |
| 25% | 29.03% | 45.97% | 8.71E−13 |
| 30% | 27.10% | 42.90% | 8E−13 |
| 35% | 25.16% | 39.84% | 7.56E−13 |
| 40% | 23.23% | 36.77% | 6.15E−13 |
| 45% | 21.29% | 33.71% | 6.38E−13 |
| 50% | 19.35% | 30.65% | 5.3E−13 |
| 55% | 17.42% | 27.58% | 4.55E−13 |
| 60% | 15.48% | 24.52% | 4.26E−13 |
| 65% | 13.55% | 21.45% | 4.09E−13 |
| 70% | 11.61% | 18.39% | 4.05E−13 |
| 75% | 9.68% | 15.32% | 3.48E−13 |
| 80% | 7.74% | 12.26% | 3.24E−13 |
| 85% | 5.81% | 9.19% | 3.12E−13 |
| 90% | 3.87% | 6.13% | 2.93E−13 |

From the above examples and comparative examples 1 to 4, it can be seen that the addition of the Al element can obviously improve the prosthesis beam quality, the specific performance is to effectively improve the advantage depth and the depth of the tumor 30 RBE-Gy. And with the increase of aluminum content, the advantage depth is increasing, and the depth of tumor 30 RBE-Gy showed a trend of increasing first and then decreasing.

From Example 1, Example 2, and Example 3, it can be seen that the prosthesis beam qualities is different at different densities with the same composition and content, and the aluminum contents corresponding to the maximum values of the depth of the tumor 30 RBE-Gy is different at different densities. Therefore, the density of the neutron moderation material also affects the prosthesis beam quality.

From Example 2 and Example 3, it can be seen that in the case of the same composition of the neutron moderation material and the different composition structure of the neutron moderation material, the improvement of the prosthesis beam quality is consistent with the increase of the content of the aluminum. Therefore, different composition forms (such as mixed homogeneous compact, stacked and sintered) have no effect on the beneficial effect of this experiment.

From the comparison of Example 4 to Example 5, it can be seen that the prosthesis beam qualities is obviously improved with increase of the aluminum element in the neutron moderation material, this shows that no matter what kind of material composition, the prosthesis beam quality can be effectively improved as long as the neutron moderation material is composed of the three elements of Mg, Al, and F.

Example 6 is carried out on the basis of Example 2. By comparing the two examples, it can be seen that the prosthesis beam quality of the neutron moderation material has been improved after adding different amounts of LiF. And as the amount of LiF increases, the improvement degree of prosthesis beam quality is also increased.

It is apparent from comparing Example 6 and Comparative example 5 that the addition of LiF can effectively reduce the amount of γ-ray in the epithermal neutron ray. Experiments prove that LiF can effectively reduce the γ-ray content under the premise of improving the prosthesis beam quality because of the existence of $^6$Li element. Therefore, the addition of $^6$Li-containing substances can improve the prosthesis beam quality and reduce the γ ray contamination in the epithermal neutron ray.

The above illustrates and describes basic principles, main features and advantages of the present disclosure. Those skilled in the art should appreciate that the above embodiments do not limit the present disclosure in any form. Technical solutions obtained by equivalent substitution or equivalent variations all fall within the scope of the present disclosure.

What is claimed is:

1. A neutron moderation material comprising:
    Mg element;
    Al element; and
    F element;
    wherein the weight percentage of the Mg element, Al element and F element accounts for the neutron moderation material is 3.5%≤Mg≤37.1%, 5.0%≤Al≤90.4%, 5.8%≤F≤67.2%, respectively; and
    the sum of the weights of the weights of the Mg, Al and F elements is 100% of the total weight of the neutron moderation material.

2. The neutron moderation material according to claim 1, wherein the neutron moderation material is added with $^6$Li-containing substances to reduce γ ray contamination, wherein the addition amount of the $^6$Li-containing substances accounts for 0.1% to 10% in percentage by weight of the neutron moderation material.

3. The neutron moderation material according to claim 1, wherein the density of the neutron moderation material is 60% to 100% of the theoretical density.

4. The neutron moderation material according to claim 1, wherein the material composition of the neutron moderation material is MgF$_2$ and Al.

5. The neutron moderation material according to claim 1, wherein the relationship between the ratio of the density of the neutron moderation material to the theoretical density and the weight percentage of Al element in the neutron moderation material is selected in the following groups: the weight percentage of the Al element to the neutron moderation material is 35%≤Al≤70% when the density of the neutron moderation material is 60% of the theoretical density; the weight percentage of the Al element to the neutron moderation material is 50%≤Al≤80% when the density of the neutron moderation material is 80% of the theoretical density; the weight percentage of the Al element to the neutron moderation material is 65%≤Al≤90% when the density of the neutron moderation material is the theoretical density.

6. The neutron moderation material according to claim 4, wherein the relationship between the ratio of the density of the neutron moderation material to the theoretical density and the weight ratio of Al to MgF$_2$ is selected in the following groups: the weight ratio of Al to MgF$_2$ is 11:9 when the density of the neutron moderation material is 60% of the theoretical density; the weight ratio of Al to MgF$_2$ is 13:7 when the density of the neutron moderation material is 80% of the theoretical density; the weight ratio of Al to MgF$_2$ is 4:1 when the density of the neutron moderation material is the theoretical density.

7. The neutron moderation material according to claim 1, wherein the neutron moderation material is disposed in a beam shaping assembly in the form of stacked or mixed powder compact or mixed powder sinter serving as a moderator of the beam shaping assembly.

8. The neutron moderation material according to claim 7, wherein the beam shaping assembly further comprises a reflector surrounding the moderator, a thermal neutron absorber adjoining to the moderator, and a radiation shield disposed within the beam shaping assembly.

9. The neutron moderation material according to claim 8, wherein the beam shaping assembly is used for accelerator-based neutron capture therapy, and the accelerator-based neutron capture therapy comprises an accelerator, a charged particle beam accelerated by the accelerator, a charged particle beam inlet for the charged particle beam passing through, a neutron generating portion for generating a neutron beam by nuclear reaction with the charged particle beam, a beam shaping assembly for adjusting the beam flux and quality of the neutron beam generated by the neutron generating portion, and a beam outlet adjoining to the beam shaping assembly, wherein the neutron generating portion is accommodated in the beam shaping assembly.

10. The neutron moderation material according to claim 2, wherein the neutron moderation material is added with LiF to reduce γ ray contamination, and wherein the addition amount of LiF is 0.1% to 10% of the total weight of the neutron moderation material.

11. A neutron moderation material comprising:
Mg element;
Al element; and
F element;
wherein the sum of the weights of the weights of the Mg, Al and F elements is 100% of the total weight of the neutron moderation material; and
the neutron moderation material is added with $^6$Li-containing substances to reduce γ ray contamination, wherein the addition amount of the $^6$Li-containing substances accounts for 0.1% to 10% in percentage by weight of the neutron moderation material.

12. The neutron moderation material according to claim 11, wherein the density of the neutron moderation material is 60% to 100% of the theoretical density.

13. The neutron moderation material according to claim 11, wherein the material composition of the neutron moderation material is MgF$_2$ and Al.

14. The neutron moderation material according to claim 12, wherein the relationship between the ratio of the density of the neutron moderation material to the theoretical density and the weight percentage of Al element in the neutron moderation material is selected in the following groups:the weight percentage of the Al element to the neutron moderation material is 35%≤Al≤70% when the density of the neutron moderation material is 60% of the theoretical density; the weight percentage of the Al element to the neutron moderation material is 50%≤Al≤80% when the density of the neutron moderation material is 80% of the theoretical density; the weight percentage of the Al element to the neutron moderation material is 65%≤Al≤90% when the density of the neutron moderation material is the theoretical density.

15. The neutron moderation material according to claim 13, wherein the relationship between the ratio of the density of the neutron moderation material to the theoretical density and the weight ratio of Al to MgF$_2$ is selected in the following groups: the weight ratio of Al to MgF$_2$ is 11:9 when the density of the neutron moderation material is 60% of the theoretical density; the weight ratio of Al to MgF$_2$ is 13:7 when the density of the neutron moderation material is 80% of the theoretical density; the weight ratio of Al to MgF$_2$ is 4:1 when the density of the neutron moderation material is the theoretical density.

16. The neutron moderation material according to claim 11, wherein the $^6$Li-containing substances are LiF.

17. A neutron moderation material comprising:
Mg element;
Al element; and
F element;
wherein the sum of the weights of the weights of the Mg, Al and F elements is 100% of the total weight of the neutron moderation material;
Mg element, Al element and F element make up the substance of Al, MgF$_2$ and AlF$_3$, and
one or more of Al, MgF$_2$ and AlF$_3$ form a moderator in the form of stacked or mixed powder compact or mixed powder sinter.

18. The neutron moderation material according to claim 17, wherein the moderator consists of Al and MgF$_2$.

19. The neutron moderation material according to claim 18, wherein the weight ratio of Al to MgF$_2$ is between 1:19 to 9:1.

20. The neutron moderation material according to claim 17, wherein the neutron moderation material is added with $^6$Li-containing substances to reduce γ ray contamination, wherein the addition amount of the $^6$Li-containing substances accounts for 0.1% to 10% in percentage by weight of the neutron moderation material.

* * * * *